United States Patent
Zwyer et al.

(10) Patent No.: US 11,207,271 B2
(45) Date of Patent: Dec. 28, 2021

(54) MAZINDOL IR/SR MULTILAYER TABLET AND ITS USE FOR THE TREATMENT OF ATTENTION DEFICIT/HYPERACTIVITY DISORDER (ADHD)

(71) Applicant: NLS-1 Pharma AG, Stans (CH)

(72) Inventors: Alexander C. Zwyer, Teufen (CH); Lewis P. Amsel, Sarasota, FL (US); Virginia Schmith, Wrightsville Beach, NC (US); Scott Brantley, Apex, NC (US)

(73) Assignee: NLS Pharmaceutics AG, Stans (CH)

( * ) Notice: Subject to any disclaimer, the term of this patent is extended or adjusted under 35 U.S.C. 154(b) by 130 days.

(21) Appl. No.: 16/083,131

(22) PCT Filed: Mar. 8, 2017

(86) PCT No.: PCT/IB2017/000352
§ 371 (c)(1),
(2) Date: Sep. 7, 2018

(87) PCT Pub. No.: WO2017/153846
PCT Pub. Date: Sep. 14, 2017

(65) Prior Publication Data
US 2021/0038521 A1    Feb. 11, 2021

Related U.S. Application Data

(60) Provisional application No. 62/305,600, filed on Mar. 9, 2016.

(30) Foreign Application Priority Data

Mar. 9, 2016   (WO) ................. PCT/EP2016/055048

(51) Int. Cl.
| | | |
|---|---|---|
| A61K 9/24 | (2006.01) | |
| A61K 9/20 | (2006.01) | |
| A61K 31/4188 | (2006.01) | |
| A61K 33/26 | (2006.01) | |
| A61K 9/00 | (2006.01) | |
| A61K 45/06 | (2006.01) | |

(52) U.S. Cl.
CPC ............ *A61K 9/209* (2013.01); *A61K 9/2095* (2013.01); *A61K 31/4188* (2013.01); *A61K 33/26* (2013.01); *A61K 9/0053* (2013.01); *A61K 45/06* (2013.01)

(58) Field of Classification Search
CPC .............................. A61K 9/209; A61K 9/2086
See application file for complete search history.

(56) References Cited

U.S. PATENT DOCUMENTS

| | | | |
|---|---|---|---|
| 4,855,440 A | 8/1989 | Shumway et al. | |
| 8,293,779 B2 | 10/2012 | Konofal | |
| 2006/0240105 A1 | 10/2006 | Devane et al. | |
| 2007/0148237 A1* | 6/2007 | McKinney | A61K 31/423 424/468 |
| 2007/0264323 A1 | 11/2007 | Shojaei et al. | |
| 2009/0175939 A1* | 7/2009 | Bosse | A61K 45/06 424/472 |
| 2009/0318520 A1 | 12/2009 | Kovacs et al. | |
| 2013/0095140 A1* | 4/2013 | Baron | A61K 9/209 424/400 |

FOREIGN PATENT DOCUMENTS

| | | |
|---|---|---|
| CN | 1579401 A | 2/2005 |
| CN | 1593404 A | 3/2005 |
| CN | 1985823 A | 6/2007 |
| CN | 104013620 A | 9/2014 |
| JP | 2003-531165 | 10/2003 |
| JP | 2013189467 A | 9/2013 |
| KR | 20070081903 A | 8/2007 |
| WO | WO/02/38133 | 5/2002 |
| WO | WO/2006/069030 A1 | 6/2006 |
| WO | WO 2011/123496 A1 | 10/2011 |
| WO | WO-2011123496 A1 * | 10/2011 ............. A61P 25/14 |

OTHER PUBLICATIONS

International Search Report and Written Opinion dated Sep. 8, 2017, in International Application No. PCT/IB2017/000352 (12 pgs.).
Mattingly et al., Optimizing outcomes in ADHD treatment: From clinical targets to novel delivery systems, CNS Spectrums (2016), 21(S1):45-59.
Swanson et al., Development of a New Once-a-Day Formulation of Methylphenidate for the Treatment of Attention-deficit/Hyperactivity Disorder, Arch Gen Psychiatry (2003), 60:204-211.
Karna et al., Formulation Approaches for Sustained Release Dosage Forms: A Review, Asian J Pharm Clin Res (2015), 8:46-53.
Nikam et al., Eudragit A Versatile Polymer: A Review, Pharmacologyonline (2011), 1:152-164, available at https://pharmacologyonline.sllae.it/front/newsletter_2011_1_ (last visited Jul. 30, 2021).
Fallingborg, Intraluminal pH of the human gastrointestinal tract, Danish Med. Bulletin (1999), 46:183-196.
Evonik Health Care, Eudragit® Functional Polymers for Oral Solid Dosage Forms, https://healthcare.evonik.com/product/health-care/en/products/pharmaceutical-excipients/EUDRAGIT/?xd_co_f=ZmU2NGYwMmItOTFjMC00ZWM0LWIwZTEtZjVhYmEwjNWFiY2Qy.
Ritalin LA Labeling-Package Insert (2013), available at https://www.accessdata.fda.gov/drugsatfda_docs/label/2013/021284s019lbl.pdf (last visited Jul. 30, 2021).

(Continued)

*Primary Examiner* — Robert A Wax
*Assistant Examiner* — William Craigo
(74) *Attorney, Agent, or Firm* — Finnegan, Henderson, Farabow, Garrett & Dunner, L.L.P.

(57) ABSTRACT

The present invention relates to a modified-release composition of mazindol and its use in the treatment of attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) in particular in children, adolescents and adults.

21 Claims, 4 Drawing Sheets

(56) References Cited

OTHER PUBLICATIONS

Adderall XR Labeling-Package Insert (2013), available at https://www.accessdata.fda.gov/drugsatfda_docs/label/2013/021303s026lbl.pdf (last visited Jul. 30, 2021).

Kim et al., Validated method for determination of mazindol in human plasma by liquid chromatography/tandem mass spectrometry, J. Chromatography B (2009), 877:1011-1016.

Lomax, Imidazoline Derived Amphoterics, Amphoteric Surfactants (1996).

Maulding et al., Solvolysis of a Substituted Imidazoline, Mazindol, Journal of Pharmaceutical Sciences (1975), 64(11):1833-38.

NLS Pharma, NLS Pharma Announces New Information in Support of the Mechanism of Action of Its Lead Compound NLS-1 Mazindol CR (May 2017), available at https://www.prnewswire.com/news-releases/nls-pharma-announces-new-information-in-support-of-the-mechanism-of-action-its-lead-compound-nls-1-mazindol-cr-300464651.html (last visited Jul. 30, 2021).

Wigal et al., A Double-Blind, Placebo-Controlled, Phase II Study to Determine the Efficacy, Safety, Tolerability and Pharmacokinetics of a Controlled Release (CR) Formulation of Mazindol in Adults with DSM-5 Attention-Deficit/Hyperactivity Disorder (ADHD), CNS Drugs, 32:289-301 (2018).

* cited by examiner

MAZINDOL IR/SR MULTILAYER TABLET AND ITS USE FOR THE TREATMENT OF ATTENTION DEFICIT/HYPERACTIVITY DISORDER (ADHD)

This application is a national stage filing under 35 U.S.C. § 371 of International Application No. PCT/IB2017/000352, filed on Mar. 8, 2017, which claims priority of U.S. Provisional Application No. 62/305,600, filed on Mar. 9, 2016, and PCT Application No. PCT/EP2016/055048, filed on Mar. 9, 2016. The contents of these applications are each incorporated herein by reference.

The present invention relates to a modified-release composition of mazindol and its use in the treatment of attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) in particular in children, adolescents and adults.

ADHD is a behavioural disorder that constitutes one of the most frequently encountered patterns in child and adolescent psychopathology. It is also present in adults. Although a recent longitudinal study raises possibility that adults presenting with the ADHD symptom picture may not have a childhood-onset neurodevelopmental disorder (Moffitt 2015), the majority of available data and scientific consensus suggest that ADHD is the same disease in both adults and paediatrics (Kooji 2010) In fact, the criteria for ADHD was changed in DSM-V (American Psychiatric Association, 2013) to more accurately characterize ADHD as a neurodevelopmental disorder, which begins in childhood but continues through adulthood for some people. In recent studies the prevalence of ADHD is estimated to be 7 to 8% of school-age children (Barbaresi 2002) and 4 to 5% of adults (Kessler 2006). Clinically, this disorder combines inattention, impulsivity and motor hyperactivity leading to impairment in academic/work, social and interpersonal functioning. Without treatment, children and adults are unable to stay on task leading to decreased academic or work performance. In addition, impulsivity may lead to decreased quality of work and dysfunctional social functioning.

The stimulants used, and commonly accepted in the pharmacological treatment of ADHD, belong to several pharmacological classes: psychostimulants (amphetamine, methylphenidate), eugregorics (armodafinil, modafinil, adrafinil), nonstimulants (atomoxetine, clonidine and guanfacine), and inhibitors of mono-amine oxydase B (selegiline). The improvement of inattention, impulsivity, and hyperactivity by such dopaminergic psychostimulants is often very significant, but nevertheless insufficient in many subjects.

Stimulants (e.g., methylphenidate or amphetamines salts) have short half-lives and require controlled release delivery in the majority of patients. Even with controlled delivery, it is difficult to maintain adequate efficacy during school (and/or work) hours and yet achieve concentrations that will allow the patient to fall asleep and remain asleep at night. Stimulants are associated with the appearance of "on-off" effects, where the coming-off effect is accompanied by a "symptom rebound" effect with a worsening of the symptoms in the early evening (e.g., a time when homework needs to be completed).

While stimulant medication is an effective treatment for many of the symptoms associated with ADHD, there are concerns about diversion of these medications for misuse and abuse, and some rare but serious cardiovascular side-effects can occur with the use of stimulant medication. Non-stimulants such as atomoxetine, clonidine and guanfacine have also been found to be efficacious in treating ADHD but the efficacy of these agents may not be comparable to that seen with stimulants (Faraone 2009). Even with stimulant treatment, optimal functioning occurs in only roughly one in four children with ADHD (Greenhill 1996). Despite considerable advances in our understanding and treatment of ADHD, the disorder remains difficult to manage and further treatment options need to be developed (Antshel 2011). In addition, some of the medications administered in the treatment of ADHD are not suited for administration to children, especially because of excessive size of the tablets or the administration of the medications several times a day.

Use of mazindol in treatment of attention deficit/hyperactivity disorder (ADHD), according to DSM-IV (or DSM-V) criteria, comprising administering an effective amount of mazindol to a patient in need of such treatment has been described in U.S. Pat. No. 8,293,779. Mazindol has the following chemical formula:

5-(4-chlorophenyl)-2,5-dihydro-3H-imadazo[2,1-a]isoindol-5-ol

Mazindol is considered, in current medication classifications, as a psychoanaleptic and anorexigenic medication. It is currently authorized in Argentina, Mexico/Central America, and Japan for use in the treatment of obesity.

The essential pharmacological action of mazindol, in all species studied, in healthy animals and in humans, is hypothalamic, on the appetite-regulating dopaminergic centres (Hadler, 1972). It is metabolized extensively and the metabolites are then mostly excreted in the urine. Mazindol is a non-amphetamine compound because of its tricyclic chemical structure. It offers a pharmacological profile very close to that of amphetamines with less abuse liability. Indeed, mazindol is not metabolised to an amphetamine-like compound, but it acts by blocking the dopamine and norepinephrine reuptake similarly to amphetamine.

In addition, in animal toxicology studies, the toxic potential of mazindol has proved to be very low In particular, no carcinogenic effect, no mutagenic effect, and no toxicology effect in reproduction was observed.

In U.S. Pat. No. 8,293,779, it is disclosed that, after single or repeated oral administration, mazindol is absorbed with a time to maximum concentrations (Tmax) of 2-4 hours. The half-life of mazindol after an immediate release formulation is 9.1±1.7 h in healthy volunteers (Kim 2009); therefore, steady-state concentrations are reached after approximately 30-55 hours. The pharmacokinetics is linear (independent of the dose) for doses of between 1 mg/day and 4 mg/day. This result however relates to current immediate-release formulations of mazindol.

Immediate-release pharmaceutical compositions of mazindol, such as Diminex®, Sanorex® and Teronac®, ensure the release of the active ingredient over a period of <1 h in vitro. Indeed, immediate-release pharmaceutical compositions of mazindol have been reported to undergo hydrolysis at moderate temperatures in neutral and alkaline aqueous solutions, including in human plasma. Due to the mild alkaline nature of plasma, improved mazindol stability in human plasma is achieved by adding acidic buffer.

Such immediate release compositions thus require twice daily administration, which limits compliance in the special case of children of school age, as the second administration is often requested to be done at midday, i.e. during school time. Even given the fact that the immediate release tablet undergoes complete in vitro dissolution within 1 hour, the time to maximum concentrations (Tmax) occurs at 3-4 hours after drug administration in healthy volunteers (Kim 2009). Rapid initial absorption will allow the earlier achievement of adequate systemic exposure to achieve desired efficacy (e.g., administer early and have onset of efficacy 1-2 hours later, when patient is at school or work).

International Publication No. WO2001/123496 to Kidane et al. (2011) discloses formulations of mazindol with the objective of having mazindol be absorbed in high pH environments, such as the colon. These formulations are primarily directed to encapsulated pellets that can be immediate release, extended release, or delayed release. The formulations disclosed in Kidane, being designed with enteric coatings to release mazindol at higher pH, such as 6.8 (see, e.g., Examples 2, 3, 9, and 12), will provide dissolution and release late in the small intestine, which would likely result in a significant portion of the drug not being released prior to reaching the colon. (Fallingborg J.). Since clinical pharmacokinetic studies have shown that mazindol is not likely to be absorbed in the colon and mazindol's solubility decreases with increasing pH (i.e., most soluble at the pH of the stomach and least soluble in the colon, particularly where water is less available due to reabsorption), these formulations likely result in a significant reduction of the availability of absorbable, dissolved mazindol.

To achieve once daily dosing regimen (a very desirable regimen), a better controlled release portion would also be needed to assure that adequate plasma concentrations are achieved throughout the day and evening, while allowing the subject to fall asleep and remain asleep during the night. Thus, there is a need for a pharmaceutical composition comprising mazindol with an improved release profile of active substance combining an immediate and a sustained release, an improved compliance for patients, and reduced fluctuation in steady-state mazindol plasma concentrations during a dosing interval.

SUMMARY

According to a first aspect, the present invention thus relates to a mazindol oral pharmaceutical unit dosage form in the form of a multilayer matrix-type tablet comprising:
  at least one immediate-release (IR) layer comprising mazindol and at least one diluent,
  at least one sustained-release (SR) layer comprising mazindol and at least one sustained-release, pH-independent and water-insoluble polymer,
for a total amount of mazindol comprised between 1 and 6 mg and a ratio in weight between the IR layers and the SR layers comprised between 40:60 and 80:20 preferably between 50:50 and 70:30, more preferably of 50:50.

The oral pharmaceutical unit dosage form in the form of a multilayer matrix-type tablet of the invention provides a rapid release of drug to achieve a rapid therapeutic blood level and a sustained release portion to provide a continual release of mazindol available for absorption into the patients' blood stream to achieve a prolonged therapeutic effect. This combination thus achieves a once daily regimen for the product. This oral pharmaceutical unit dosage form has the following advantages:
  Ease of swallowing;
  Ease of manufacture;
  The ability to control the release rate of the drug by modifying the components of each separate layer;
  Superior stability compared to other dose forms, such as capsules, liquids;
  Prevents patient tampering with the dose form;
  Reduced fluctuation in steady-state mazindol plasma concentrations during a dosing interval;
  Enhanced stability;
  Onset within 1-2 hours, while not unnecessarily delaying consumption of food; and
  Muted increase in heart rate.

According to another aspect, the invention relates to a process for preparing the unit dosage form according to the invention, comprising the following steps:
  (a) preparing the blend of the excipients of the IR layers,
  (a') preparing the blend of the excipients of the SR layers,
  (b) adding the IR blend of step (a) and the SR blend of step (a') into a multilayer, preferably a bilayer, tablets' press.

According to a further aspect, the invention relates to the unit dosage form according to the invention, for its use as medicinal product administered in repeat once-a-day form via oral route.

According to a further aspect, the invention relates to the unit dosage form according to the invention, for use for treating attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) in particular in children, adolescents and adults.

According to a further aspect, the invention relates to a method for treating attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) comprising the administration, preferably in repeat once-a-day via oral route, of the unit dosage form according to the invention to a patient in need thereof, in particular in children, adolescents and adults.

According to a further aspect of the present invention, the invention relates to the unit dosage form according to the invention, used in combination with iron as a combination product for simultaneous, separate or sequential use, in particular for treating attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) in particular in children, adolescents and adults.

According to a further aspect, the invention relates to a method for treating attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) comprising the administration, preferably in repeat once-a-day via oral route, of the unit dosage form according to the invention and the administration of iron to a patient in need thereof, in particular in children, adolescents and adults.

According to a further aspect of the present invention, the invention relates to the unit dosage form according to the invention, used in combination with a psychostimulant as a combination product for simultaneous, separate or sequential use, in particular for treating attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) in particular in children, adolescents and adults.

According to a further aspect, the invention relates to a method for treating attention deficit disorders (ADD) or attention deficit/hyperactivity disorder (ADHD) or related deficit of alertness (i.e., incoercible sleepiness) or decline of vigilance (i.e., daytime somnolence) or excessive daytime sleepiness (e.g., narcolepsy, idiopathic hypersomnia) comprising the administration, preferably in repeat once-a-day, via oral route of the unit dosage form according to the invention and the administration of a psychostimulant to a patient in need thereof, in particular in children, adolescents and adults.

Definitions

The term "matrix-type tablet" is used in the invention to designate a tablet whose inner structure in each layer is homogeneous and identical from the center towards the periphery of the layer. Therefore, the layers of the tablets of the present invention consist of a homogeneous mixture of active ingredient in powder or granule form and of a compression matrix.

The term "compression matrix" in the present invention is used to designate all the excipients which take part in the cohesion of the tablet. Said compression matrix is both water-insoluble and has a certain permeability (hydrophilic matrix) or porous network (inert matrix) responsible for the sustained release of the active ingredient, which does not vary in relation to the pH conditions of the medium. The term "compression mixture" is used in the present application to designate all the constituents of the tablets (the active ingredient(s), granulated or not, and the constituents of the compression matrix) before its compression in tablet form.

As used in the present invention, the term "Cmax" refers to the maximum concentration in the plasma after a single dose and Cmax(ss) refers to the Cmax at steady-state. The Cmax and Cmax(ss) are lower with this controlled release formulation.

As used in the present invention, the term "steady-state" refers to the concentrations in the body after 4 to 7 half-lives after repeat dosing. The concentrations at steady-state differ depending on the formulation used and the dosing frequency. At steady state, plasma concentrations of mazindol will vary between Cmax(ss) and Cmin(ss) (the minimum observed concentration at steady-state).

A study with repeat doses not only provides a measure of the usual pharmacokinetic parameters (area under the curve during a dosing interval at steady-state, $AUC(0-\tau)$, Cmax(ss), the time to the Cmax or Cmax(ss), Tmax), but also demonstrates the significance of the fluctuations between the steady-state peak (Cmax(ss)) and trough (Cmin(ss)) concentrations.

Tmax is the time to reach the peak concentration. This value is dependent on the absorption rate of a pharmaceutically active material. The pharmacokinetic parameters Cmax, Cmax(ss), and Tmax result directly from experimental plots. Repeat dosing with a drug can involve a certain accumulation of the drug, or its metabolites, the significance of which depends on the dosage schedule used.

Given a drug M, administered orally at a dose D at a dosing time interval T. As the drug is given before the previous dose is fully eliminated, the amount administered adds to the non-eliminated amount from the previous doses (superimposition principle). After a period of 4-7 half-lives, the amount of drug absorbed that enters the body is equivalent to the amount that is eliminated from the body and steady state is achieved. Concentrations vary between a trough concentration Cmin(ss) and a peak concentration Cmax(ss). As used in the present invention, "repeat oral dosing" refers to administration of the formulation of the present invention at a dose D at a dosing time interval $\tau$ of between 20 and 24 hours.

The "fluctuation" and "swing" parameters are expressed as a % and are calculated according to the following equations:

$$\text{Fluctuation: } 100\% \, (Cmax(ss)-Cmin(ss))/Cav$$

wherein Cav is the "average steady-state concentration", representing the $AUC(0-\tau)$ divided by the dosing interval: $Cav=AUC(0-\tau)/\tau$.

In the meaning of the present invention, the expression «reduction of fluctuations» may designate the lowering of the difference between the Cmax(ss) and Cmin(ss) or differences between the peaks and troughs, or preferably a value for the «fluctuation» parameter of between 25% and 75% in one embodiment, <60% in one embodiment, <50% in one embodiment, or more preferably less than 35%.

$$\text{Swing: } 100*(Cmax(ss) \, Cmin(ss))/Cmin(ss)=\Delta$$

The half-life ($t\frac{1}{2}$) is the time for a concentration C of a drug in a body fluid or a tissue to reach the concentration C/2.

The area under the curve during a dosing interval at stead-state, $AUC(0-\tau)$, corresponds to the integral of the plasma concentration over a given dosing interval. The $AUC(0-\tau)$ is expressed in units of mass (mg, ng)×liter (or $mL)^{-1}$×hour, and is dependent on the bioavailability and clearance of a drug.

In the meaning of the present invention, by a profile having «reduced fluctuation» is meant a profile having a swing A of less than 50% in one embodiment or <60% in one embodiment, or <35% in one embodiment.

In the meaning of the present invention, by a profile having «reduced fluctuation» is also meant a plasma profile maintained above 40% or preferably above 50% of the Cmax(ss) value for at least 12 hours.

An "immediate-release (IR) layer" refers to a layer that releases greater than or equal to about 80% by weight of mazindol in less than or equal to about 1 hour.

A "sustained-release (SR) layer" means a layer in which mazindol is released at a rate slower than that of an IR layer.

FIGURES

FIGS. 1-6 depict dissolution profiles of the prototype tablets of Example 3.

DETAILED DESCRIPTION

The pharmaceutical composition according to the present invention is a mazindol oral pharmaceutical unit dosage form in the form of a multilayer matrix-type tablet comprising:
at least one immediate-release (IR) layer comprising mazindol and at least one diluent,
at least one sustained-release (SR) layer comprising mazindol and at least one sustained-release, pH-independent and water-insoluble polymer,
for a total amount of mazindol comprised between 1 and 5 mg and a ratio in weight between the IR layers and the SR layers comprised between 40:60 and 80:20 preferably between 50:50 and 70:30, more preferably of 50:50. Preferably, the unit dosage form according to the invention is a bilayer tablet.

In an embodiment of formulation of the invention, the dissolution of mazindol can be between 60% and 80% at 1 hour and between 70% and 90% at 2 hours, as measured in accordance with the rotating blade method at 50 rpm according to the US Pharmacopeia Method 2, in a dissolution medium 0.01N HCl, 500 mL. In another embodiment, a unit dosage form according to the invention can have a dissolution of 50%-65% at 0.5 hours, 55%-85% at 1 hour, 65%-95% at 2 hours, not less than 75% at 4 hours, and not less than 85% at 8 hours.

Preferably, the unit dosage form according to the invention is of between 50 and 200 mg, preferably of 100 mg. Preferably, the unit dosage form according to the invention comprises between 2 and 5 mg of mazindol, preferably of between 1 and 3 mg, more preferably of 4 mg.

Preferably, the unit dosage form according to the invention maintains the steady-state mazindol plasma concentrations obtained in vivo with a reduced fluctuation of above 40% of the Cmax(ss) value, preferably above 50% of the Cmax(ss) value, and preferably above 60% of the Cmax(ss) for at least 12 h.

Examples of diluents include: lactose, monohydrate lactose, anhydrous lactose, spray-dried lactose, calcium carbonate, calcium sulfate, calcium sulfate dehydrate, calcium lactate trihydrate, monobasic calcium sulfate monohydrate, calcium carbonate, tribasic calcium phosphate, diabasic calcium phosphate, compressible sugars, dextrates, dextrin, dextrose, calcium phosphate, kaolin, magnesium carbonate, magnesium oxide, maltodextrin, mannitol, powdered cellulose, starch, modified starch, starch hydrolyzates, pregelatinized starch, microcrystalline cellulose, powdered cellulose, cellulose and cellulose derivatives, hydroxypropylmethylcellulose, hydroxypropylmethylcellulose and sucrose, preferably lactose, anhydrous lactose, spray-dried lactose, microcrystalline cellulose, powdered cellulose, cellulose and cellulose derivatives.

Diluent concentration in the IR layers can be varied between 1 and 95%, preferably 30 and 60%, more preferably 45 to 55% by weight of the total weight of the IR layers.

Preferably, a unit dosage form according to the invention comprises a lubricant in each layer.

Lubricants and glidants can be employed in the present application to prevent, reduce or inhibit adhesion or friction of ingredients of the composition. They facilitate the compression and ejection of compressed compositions from a desired die. They are compatible with the ingredients of the pharmaceutical composition, and they do not significantly reduce the solubility, hardness, chemical stability, physical stability, or the biological activity of the pharmaceutical composition. The pharmaceutically acceptable lubricants and glidants for the present application are selected from the group including but not limited to stearic acid, metallic stearates, zinc stearate, magnesium stearate, magnesium trisilicate, calcium hydroxide, tribasic calcium phosphate, magnesium carbonate, magnesium oxide, calcium stearate, glyceryl monostearate, waxes, glycerides, glyceryl behenate, glyceryl palmitostearate, silicone oil, hydrogenated vegetable oil, hydrogenated castor oil, light mineral oil, mineral oil, polyethylene glycol, methoxypolyethylene glycol, sodium acetate, sodium oleate, sodium chloride, leucine, sodium benzoate, alkyl sulfates, sodium lauryl sulfate, sodium stearyl fumarate, talc, colloidal silica, corn starch, powdered cellulose, and/or boric acid. The preferred range of lubricants/glidants is from 0% to 1% w/w of the layer.

The sustained-release, pH-independent and water-insoluble polymer in SR layers of the tablets according to the invention is selected in the group consisting of cellulose polymers, high-molecular-weight polymers of acrylic acid that are crosslinked with either allyl sucrose or allyl ethers of pentaerythritol (Carbopol, Carbomers), polymers from the class of methacrylic acids, polyvinylalcohol derivatives, polymers of lactic and glycolic acids (PLGA), starches, waxes, polyvinyl acetate derivatives, polyvinyl pyrrolidone derivatives and mixtures thereof, preferably is selected in the group consisting of cellulose polymers and high-molecular-weight polymers of acrylic acid that are crosslinked with either allyl sucrose or allyl ethers of pentaerythritol (Carbopol, Carbomers).

Cellulose polymers include hydroxypropyl methylcellulose (HPMC), hydroxypropyl cellulose (HPC), sodium CMC, ethyl cellulose derivatives such as cellulose acetate, cellulose acetate butyrate, cellulose acetate cellulose propionate, hydroxypropylmethylcellulose acetate succinate, microcrystalline cellulose (for example such as the one supplied under the trade mark Avicel®, and ethylcellulose (for example the one supplied under the trade mark Aqualon® ethylcellulose).

Polymers from the class of methacrylic acids include the grades Eudragit®RL 12.5, RL PO and RL 100 and RS 12.5, RS PO and RS 100. Starches include natural starches e.g. corn starches and modified starches such as pre-gelled starch. Waxes include white or yellow beeswax, polyvinyl acetate derivatives.

Sustained-release, pH-independent and water-insoluble polymer concentration in the SR layers can be varied between 80 and 99%, preferably 90 to 97% by weight of the total weight of the SR layers.

The unit dosage form according to the invention can include anti-agglomerant agents. anti-agglomerant agents used in the present invention include talc, silicon dioxide and its derivatives, acrylic esters, castor oil derivative, cellulose compounds, iron oxides, magnesium stearate, stearic acid and or sodium stearate.

Layers of the tablet according to the present invention can comprise a binder. Binders according to the invention, include hydroxypropylmethylcellulose (HPMC), hydroxypropylcellulose (HPC), maltodextrin, polyvinylpyrrolidone (PVP) and or microcrystalline cellulose.

The compression matrix can advantageously include, additionally to the excipients of the compression matrix, one or more excipients intended either to promote the proper conducting of the compression process.

A metabolite of mazindol, referred to as 2-(2-aminoethyl)-3-(p-chlorophenyl)-3-hydroxyphthalimidine or 2-(p-Chlorobenzoyl)-N-2-(aminoethyl)benzamide), has a Cmax that is approximately ¼ that of mazindol and a half-life that is longer than mazindol. It may accumulate and contribute to the efficacy of mazindol, particularly at steady-state. A dose of 0.25 mg to 12 mg of this metabolite may be used in the treatment of narcolepsy or ADHD.

The invention also relates to a process for preparing the unit dosage form according to the invention, comprising the following steps:
(a) preparing the blend of the excipients of the IR layers,
(a') preparing the blend of the excipients of the SR layers,
(b) adding the IR blend of step (a) and the SR blend of step (a') into a multilayer, preferably a bilayer, tablet press.

Mazindol undergoes hydrolysis at moderate temperatures with minimal amount of water. Elimination of water in a mazindol formulation therefore provides better stability. In preparing a unit dosage of the invention, preferably no water is added to the process. In one aspect of this invention, a mazindol formulation is provided that is substantially free of water, such that the amount of water by weight is less than 1.5%, 1%, or preferably less than 0.5%. Because the preferred process for formulating the bilayer or multilayer tablets of the present invention does not use water, it effectively eliminates moisture and consequently provides better stability to the bilayer or multilayer tableted formulations of the present invention. Moreover, the bilayer or multilayer design of the present invention provides better homogeneity and less variation in tablet uniformity to deliver consistency in the amount of the mazindol in the tablet and ultimately administered.

In the context of the present invention, the diagnosis of attention-deficit/hyperactivity disorder (ADHD) is based on the clinical characteristics defined by the international classification used by ICD-10 (International Classification of Diseases (ICD). World Health Organization) and DSM-V (Diagnostic and Statistical Manual of Mental Disorders, $5^{th}$ edition).

The criteria of DSM-V includes three dimensions (inattention, impulsivity and hyperactivity), normal intellectual efficiency (IQ>80) and having isolated iron deficiency, but not anaemic, that is to say having a normal haemoglobin level. The expression "iron deficiency" means hypoferrinaemia without significant modification to the serum concentration of soluble transferrin receptors.

"ADHD symptom" designates in particular attention disorders such as inattention, impulsivity, impatience, oppositional disorders, but also daytime or night-time motor hyperactivity, restless legs syndrome, and insomnia.

Insomnia designates:
a. onset insomnia that is characterised by difficulties in falling asleep;
b. maintenance insomnia that is characterised by night-time motor hyperactivity and waking up during the night, and
c. psychopathological insomnia, generally chronic and generally linked to anxiety, stress and depressive episodes.

The criteria for evaluating the efficacy of the treatment of attention-deficit/hyperactivity disorder by of the modified-release pharmaceutical composition comprising mazindol optionally in association with iron and/or a psychostimulant in the treatment of attention-deficit/hyperactivity disorder according to the present invention are the reduction (>30%) in the rating scale severity score for attention-deficit/hyperactivity symptoms AHD-RS (after 12 weeks of treatment, and an improvement in severity scores for Conner's Parent questionnaire (CPRS), Conner's Teacher questionnaire (CTRS) and CGI (clinical global impressions). Subjective somnolence is assessed using the CASS scale (child and adolescent somnolence scale). The quality of falling asleep is assessed by means of the restless legs syndrome severity scale.

The patient according to the invention is chosen from among a newborn baby, a child, an adolescent and an adult. According to a preferred embodiment, the patient is a child or an adolescent or an adult, even more preferably a child aged approximately 5 to 12 years. The patient according to the invention advantageously suffers iron deficiency, but is not anaemic. Ferritin deficiency can be measured in the serum, but also in all other biological fluids such as the cerebrospinal fluid.

A ferritin deficiency corresponds to a serum concentration of ferritin in the adult patient of less than approximately 50 μg/litre. This deficit of iron storage" (expressed by a low ferritin level) may reach ferritin concentrations of less than approximately 40 μg/l, or even less than approximately 35 μg/l, less than 30 μg/l, less than 20 μg/l, less than 15 μg/l, or even less than approximately 10 μg/l. The techniques of determining serum ferritin are well known to persons skilled in the art. The immunoenzymatic method (IMX ferritin kit, Abbot Laboratories) can be cited.

The patient according to the invention also has a normal serum concentration of receptors soluble to transferrin. Transferrin is involved in the acquisition of iron by the cells of the organism; this acquisition is controlled by the number of transferrin receptors existing on the cell surface. The concentration of these receptors can be evaluated by techniques known to persons skilled in the art such as nephelemetry (Ruivard et al. 2000 Rev Méd Interne 21: 837-843). A normal range of concentration of receptors soluble to transferrin is 2.0-4.50 mg/l for men and 1.80-4.70 mg/l for women (see RsTF kit Ref 2148315 from Roche).

According to another aspect of the present invention, mazindol is used in combination with iron as a combination product for simultaneous, separate or sequential use.

According to a preferred method of use, the iron is used as a supplement with the patient before the administration of mazindol. Within the meaning of the present invention, "iron" means iron in the form of an iron atom, iron salt or organic iron, or any formulation containing iron that is pharmaceutically acceptable. By way of a non-exhaustive list, the pharmaceutically acceptable iron salt is selected from ferrous salts and ferric salts, preferably from ferric ammonium citrate, ferric pyrophosphate, ferrocholinate, ferrous abscorbate, ferrous aspartate, ferrous chloride, ferrous sulphate, ferrous tartrate, ferrous fumarate, ferrous gluconate, ferrous gluceptate, ferrous sulphate glycine, ferrous lactate, ferrous oxalate and ferrous succinate.

According to a preferred embodiment of the invention, the iron salt is ferrous sulphate, and preferably gastro-protected ferrous sulphate.

Alternatively, the pharmaceutical acceptable iron is in the form of dextran iron, sucrose iron, poly-maltose iron, or sorbitol iron. When the iron is in the form of pharmaceutically acceptable organic iron, it is preferably iron biglycinate, iron glycinate or iron protein succinylate.

According to a preferred embodiment, the use of mazindol possibly in association with the iron according to the invention is implemented in combination with at least one compound selected from psychostimulants, as a combination product for simultaneous, separate or sequential use.

Psychostimulant compounds designate dopamine and/or noradrenaline uptake inhibitors and agonists of catecholamines. Among these, the following can be cited non-exhaustively:

1) psychostimulant compounds: methylphenidate (speciality Ritalin®, Concerta®, Equasym®, Quasym, Medikinet Retard®), armodafinil (Nuvigil®), modafinil (Sparlon®, Modiodal®, Provigil®), atomoxetine (Strattera®), bupriopion, and amphetamines such as d-amphetamine, dexedrine, dexamphetamine and lisdexamfetamine (Vyvanse®, Elvanse®).

2) L-Dopa: Modopar, Sinemat 3) selective dopamine agonists: pramipexole (Sifrol®, Mirapex®), ropinirole (Requip®, Adartrel®), lisuride, pergolide, cabergoline, etc.

In particular, when mazindol is used in association with ferrous sulphate, the quantity of ferrous sulphate administered to the patient on a daily basis is between 0.1 mg and 10 mg, preferably between 100 mg and 2 g per day, preferably approximately 500 mg, in one or more doses.

More particularly, according to the present invention, the patients undergo iron supplementation, in particular ferrous sulphate, for 12 weeks and the treatment with mazindol for 12 weeks.

According to the present invention, the composition may also comprise iron or one of its pharmaceutically acceptable salts and/or a psychostimulant.

In an embodiment of the invention, a controlled release formulation of mazindol is provided containing immediate and sustained release layers in a layered tablet, which when ingested leads to an initial burst of mazindol followed by a slower, continual release, for example, over 6-8 hours (from ingestion) where it can be dissolved and absorbed in the small intestine, before it reaches the colon. The initial availability of mazindol is advantageous for ADHD patients because they need a sufficient level of mental alertness and acuity at the beginning of their day so that they can concentrate, for instance, on work or driving to work. Subsequently, the slower continual release and absorption of mazindol in the intestine provided by the formulation of the present invention assures that adequate plasma concentrations are achieved throughout the day and evening (e.g., for completion of the workday or homework), while allowing the subject to fall asleep and remain asleep during the night.

Data using the in vitro TIM gastrointestinal system (a dynamic, multi-compartmental system simulating the human stomach and small intestines for studying the behavior of oral dosage strengths under various physiological gastrointestinal conditions) showed that the amount of mazindol that is bioaccessable, when formulated according to the present invention, is similar under fasted and fed conditions; however, the Tmax in the fed state is delayed, compared to the fasted state, by one hour or more, suggesting a food effect for mazindol. If a rapid onset is sought, one would expect from these data that a patient may have to wait about 2 hours after administration of mazindol before having breakfast. Advantageously, however, using the formulation of the present invention in vivo, mazindol can be taken at significantly less time before consuming a meal (e.g., 30 minutes) and still obtain an initial high release of mazindol in the stomach while not having to unnecessarily delay eating yet have a Tmax in the fed state that is not later than in the fasted state. As discussed, this is particularly beneficial for ADHD patients, for this initial amount of mazindol provided increases patients' mental alertness and acuity at the start of their day (e.g., driving to work, starting school).

Konofal (2014) reported that there was no relationship between Cmax of mazindol and efficacy or safety in children with ADHD. Unexpectedly, a lower Cmax after administration of a mazindol formulation of the present invention can lead, without compromising efficacy, to a muted increase in the heart rate compared to administration of, for example, an immediate release formulation of mazindol. If the Cmax after administration of a formulation of the present invention is 20% to 40% lower than the Cmax after administering an immediate release formulation of mazindol, the increase in heart rate associated with mazindol administration could surprisingly and unexpectedly be 4 to 11 beats/min less with the formulation of the present invention. This is a clinically relevant and significant outcome.

EXAMPLES

Example 1: Conditions for the Dissolution Profiles

Dissolution Medium: 0.01N HCl
Medium Volume: 500 mL
USP Apparatus 2 (Paddles)
Speed: 50 rpm
Medium Temperature: 37° C.±0.5° C.
Test 6 tablets (unless otherwise specified)
Timepoints: 1, 2, 4, 6, and 8 hours
Sample approximately 5 mL from each vessel using a syringe or autosampler with cannulae and a 10 µm full flow filter attached.

Example 2: Process for Manufacture of Mazindol Bilayer Tablets

A, Manufacturing process for the sustained release (SR) layer (2 mg. tablet)

1. Weigh the following ingredients: concentration w/w %

| | |
|---|---|
| a. Mazindol | 2.0 |
| b. Lactose monohydrate NF/hypromellose NF (Retalac ®) | 97.0 |
| c. Carbopol 971P | 0.5 |
| d. Magnesium stearate | 0.5 |
| Total = | 100% |

2. Screen ingredients a, b, c, from step 1 into the V blender and blend for 20 minutes.
3. Pass the ingredients from Step 2 through the Comil.
4. Add the ingredients from Step 3 into the V blender.
5. Screen item d from Step 1 into the blender and blend for 5 minutes,
6. Collect material from Step 5 for tablet manufacture.

B. Manufacturing process for the immediate release (IR) layer (2 mg) tablet:

1. Weigh the following ingredients: concentration w/w %

| | |
|---|---|
| a. Mazindol | 2.0 |
| b, Lactose monohydrate, NF | 97.5 |
| c. Magnesium stearate | 0.5 |
| Total = | 100% |

2. Screen ingredients a, b, from Step 1 into the V blender and blend for 20 minutes 3. Pass ingredients from Step 2 through the Comil 4. Add ingredients from Step 3 into the V blender.

5. Screen item c from Step 1 into the blender and blend for 5 minutes.

6. Collect material from Step 5 for tablet manufacture.

C. Tablet manufacture:

1. Set bilayer press for correct weight.

2. Add the IR blend to hopper 1.

3. Add the SR blend to hopper 2.

4. Compress tablets to a total weight of 100 mg.

Example 3: Dissolution Profiles of the Bilayer Tablets of Example 2

6 bilayer tablets have been prepared. Dissolution was performed per USP monograph for Mazindol tablets.

Data was collected using Pion Rainbow UV probes on n=3 tablets per batch. % Release values are reported as the average of either two or three tablets per prototype batch.

The bilayer tablet formulations are based on two sustained release (SR) formulations and one immediate release (IR) formulation.

The IR formulation is combined at three mass/mass ratios (IR/SR=50/50, 60/40, & 70/30) with each SR formulation to create 6 bilayer tablet prototypes.

The quantitative formulations for each of the prototype tablets are given in tables 1 and 2 along with their R&D batch number designation.

Figure 1:
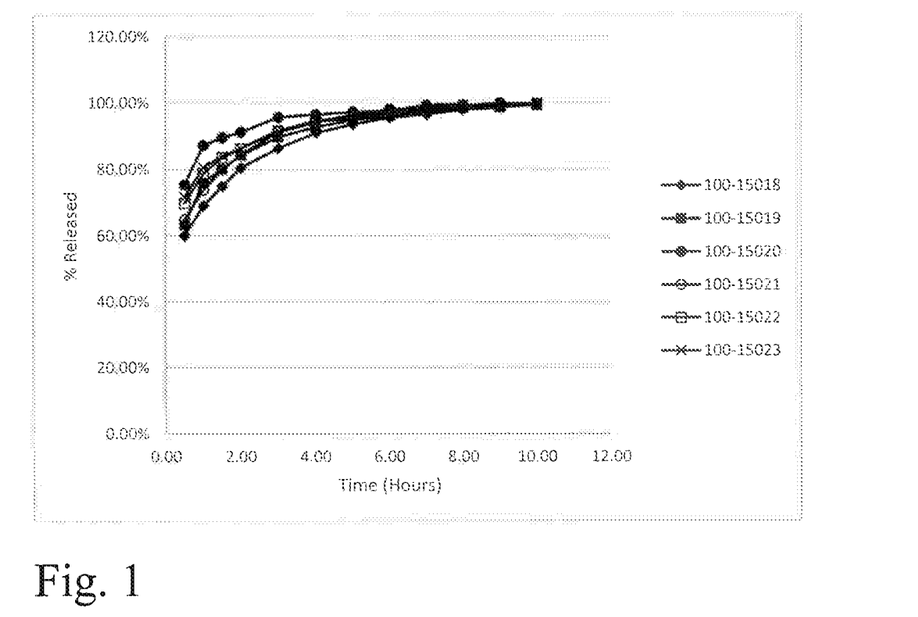
FIG. 1: Overlay of All Dissolution Profiles
Figure 2:
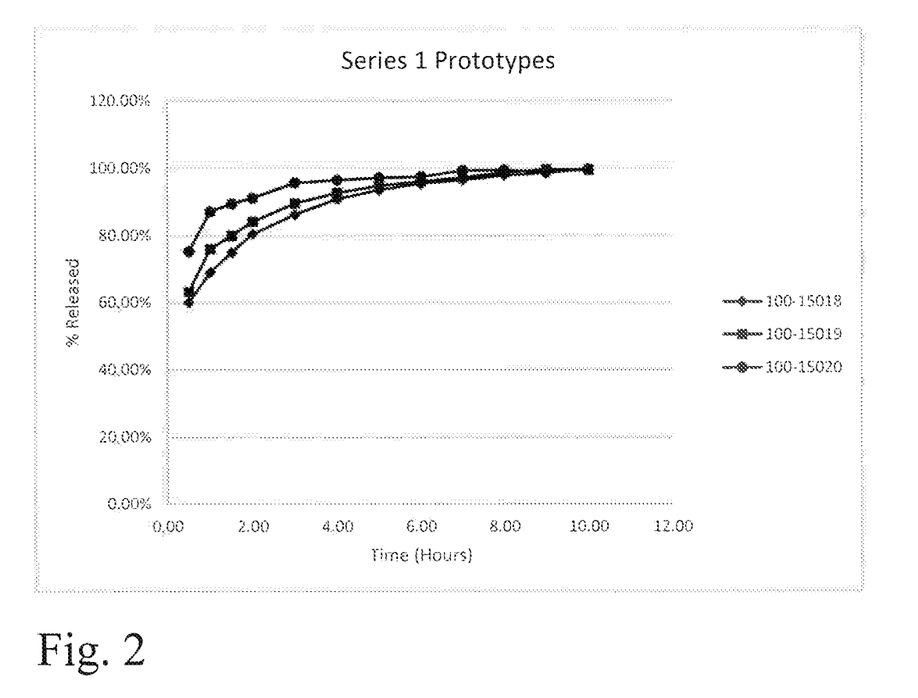
FIG. 2: Overlay of Series 1 Formulations

Table-1 formulations include the SR formulation which utilizes HPMC and Carbopol 971P to modulate Mazindol dissolution and are categorized as Series 1 prototype formulations.

Figure 3:
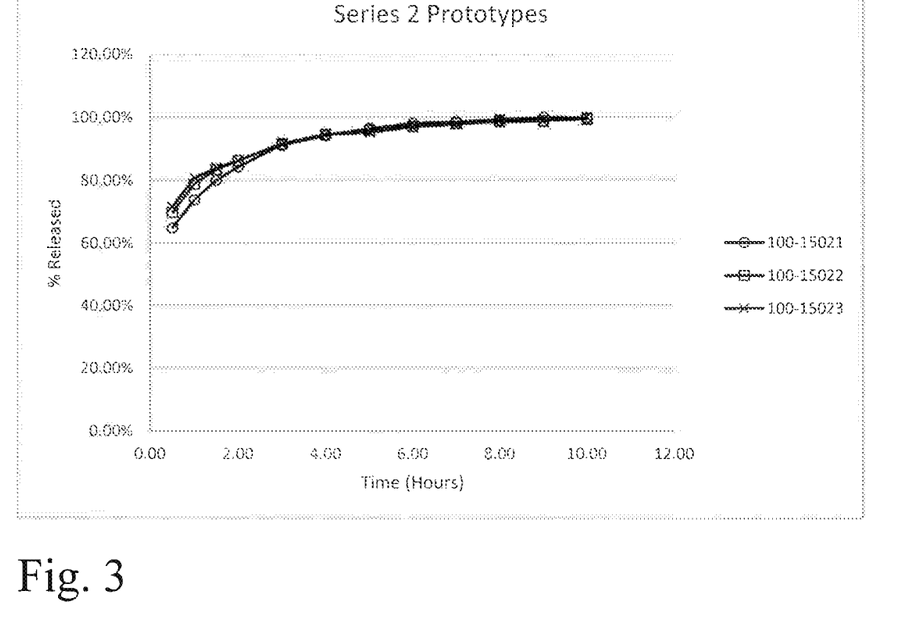
FIG. 3: Overlay of Series 2 Formulations
Figure 4:
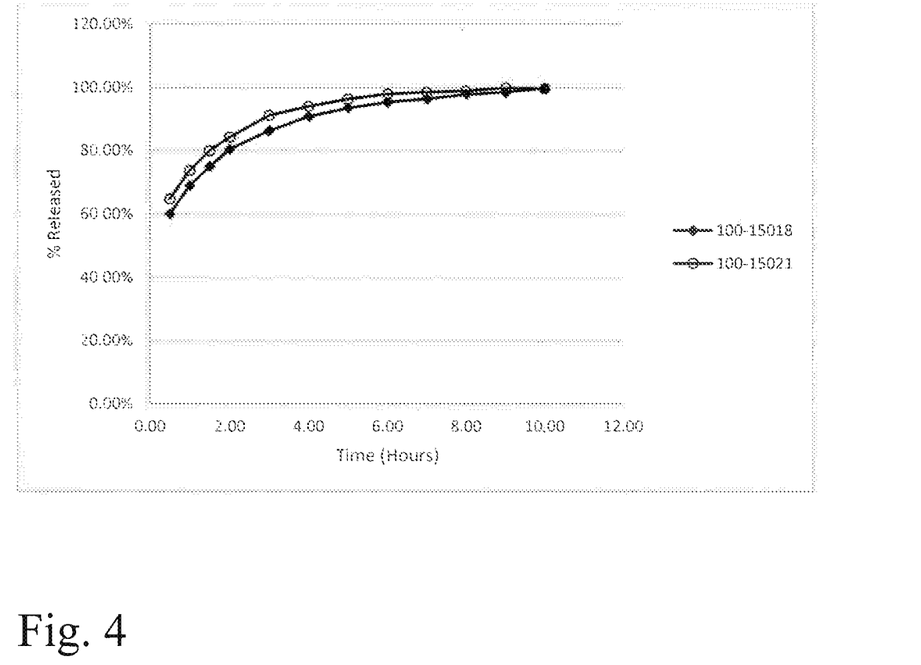
FIG. 4: Overlay of Dissolution Profiles for 50/50 IR/SR Ratio Tablet Formulations
Figure 5:
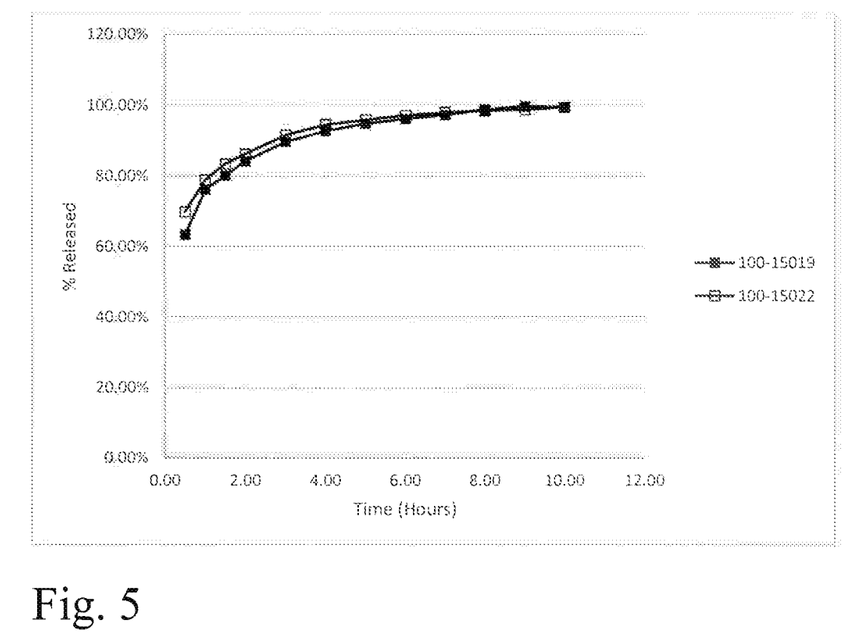
FIG. 5: Overlay of Dissolution Profiles for 60/40 IR/SR Ratio Tablet Formulations
Figure 6:
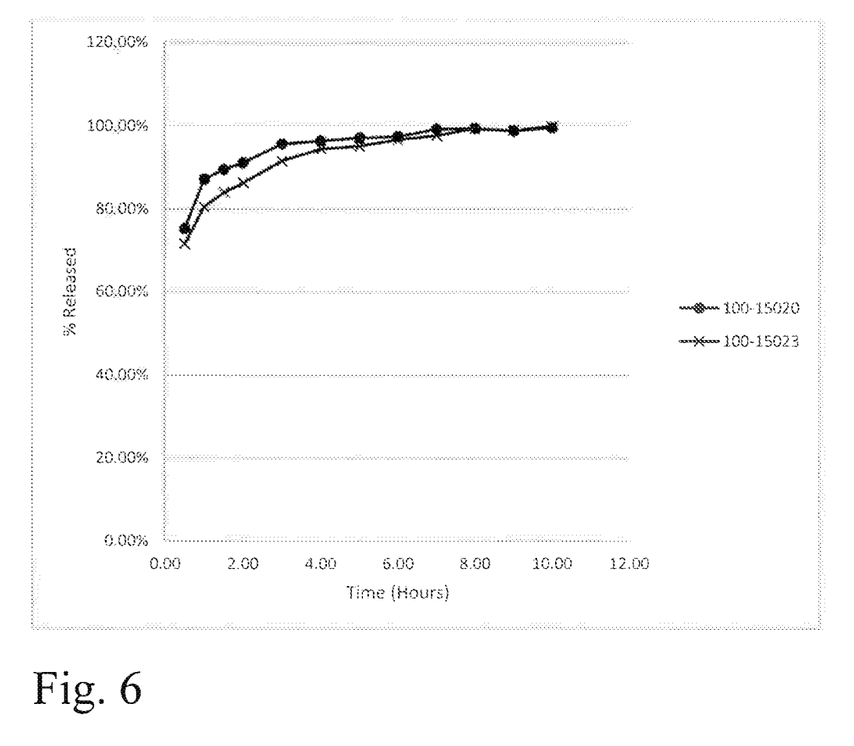
FIG. 6: Overlay of Dissolution Profiles for 70/30 IR/SR Ratio Tablet Formulations

Table-2 formulations include the SR formulation which incorporates two different molecular weight grades of HPMC to modulate Mazindol dissolution and are categorized as Series 2 prototype formulations.

Table-3 reports the dissolution testing results for each of the prototype formulations.

TABLE 1

Series 1 Prototype Tablet Formulations

| Ingredients | Batch Number | | |
|---|---|---|---|
| | 100-15018 | 100-15019 | 100-15020 |
| | IR layer/SR layer Ratio | | |
| | 50/50 mg/Tablet | 60/40 mg/Tablet | 70/30 mg/Tablet |
| IR Layer Formulation | | | |
| Mazindol | 0.5 | 0.6 | 0.7 |
| Lactose Monohydrate | 49.25 | 59.1 | 68.95 |
| Magnesium Stearate | 0.25 | 0.3 | 0.35 |
| SR Layer Formulation | | | |
| Mazindol | 0.5 | 0.4 | 0.3 |
| Lactose/HPMC K4M (Retalac ®) | 49 | 39.2 | 29.4 |
| Carbopol 971P | 0.25 | 0.2 | 0.15 |
| Magnesium Stearate | 0.25 | 0.2 | 0.15 |

TABLE 2

Series 2 Prototype Tablet Formulations

| Ingredients | Batch Number | | |
|---|---|---|---|
| | 100-15021 | 100-15022 | 100-15023 |
| | IR layer/SR layer Ratio | | |
| | 50/50 mg/Tablet | 60/40 mg/Tablet | 70/30 mg/Tablet |
| IR Layer Formulation | | | |
| Mazindol | 0.5 | 0.6 | 0.7 |
| Lactose Monohydrate | 49.25 | 59.1 | 68.95 |
| Magnesium Stearate | 0.25 | 0.3 | 0.35 |
| SR Layer Formulation | | | |
| Mazindol | 0.5 | 0.4 | 0.3 |
| Lactose/HPMC K4M (Retalac ®) | 36.75 | 29.4 | 22.05 |
| HPMC K100M | 12.5 | 10 | 7.5 |
| Magnesium Stearate | 0.25 | 0.2 | 0.15 |

TABLE 3

Dissolution Results for Prototype Tablet Batches (UV Probe Analysis Data)

| | Batch # | | | | | |
|---|---|---|---|---|---|---|
| | 100-15018 | 100-15019 | 100-15020 | 100-15021 | 100-15022 | 100-15023 |
| | Formulation | | | | | |
| | Series 1 | | | Series 2 | | |
| | IR/SR Ratio | | | | | |
| Time (Hours) | 50/50 % Released | 60/40 % Released | 70/30 % Released | 50/50 % Released | 60/40 % Released | 70/30 % Released |
| 0.5 | 60.07% | 63.29% | 75.33% | 64.81% | 69.79% | 71.62% |
| 1 | 69.01% | 76.04% | 87.15% | 73.78% | 78.84% | 80.63% |
| 1.5 | 74.97% | 80.03% | 89.50% | 80.00% | 83.40% | 83.91% |
| 2 | 80.47% | 84.20% | 91.17% | 84.32% | 86.23% | 86.29% |
| 3 | 86.31% | 89.64% | 95.69% | 91.21% | 91.58% | 91.63% |
| 4 | 90.87% | 92.71% | 96.48% | 94.11% | 94.52% | 94.44% |
| 5 | 93.57% | 94.78% | 97.19% | 96.40% | 95.85% | 95.21% |
| 6 | 95.47% | 96.13% | 97.49% | 98.03% | 97.09% | 96.81% |
| 7 | 96.48% | 97.27% | 99.30% | 98.58% | 97.92% | 97.72% |
| 8 | 97.92% | 98.80% | 99.45% | 99.06% | 98.50% | 99.39% |
| 9 | 98.57% | 99.61% | 98.84% | 99.91% | 98.77% | 98.94% |
| 10 | 99.87% | 99.44% | 99.65% | 99.77% | 99.36% | 100.00% |

Figure 7:
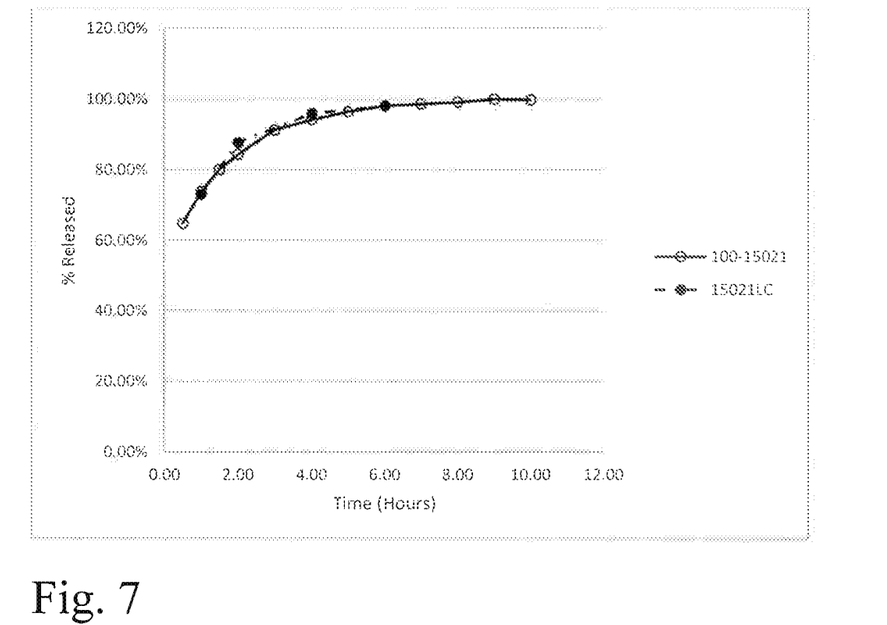
FIG. 7: Overlay of Dissolution Profiles from Batch 100-15021 Tablets Analyzed Using UV Probes (100-15021) and HPLC Analysis (15021LC)
Figure 8:
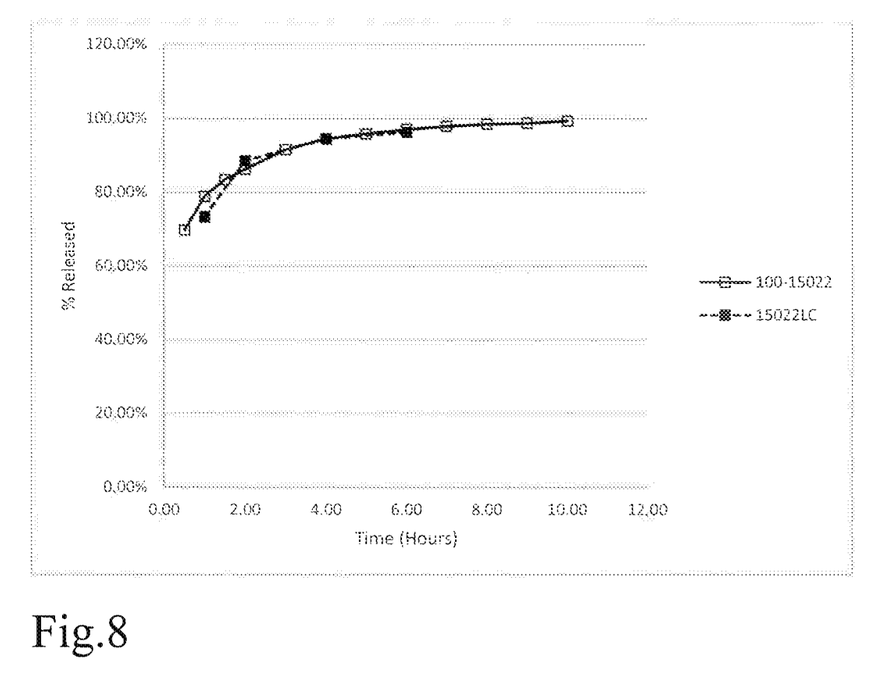
FIG. 8: Overlay of Dissolution Profiles from Batch 100-15022 Tablets Analyzed Using UV Probes (100-15022) and HPLC Analysis (15022LC)

All prototype tablet batches were tested in two distinct dissolution runs, one n=3 run analyzed using the UV probes and one n=4 run using HPLC analysis.

Table-4 reports the results for the n=3, UV analyzed dissolution testing compared to the n=4, HPLC analyzed dissolution testing for batches 100-15021 and 100-15022.

TABLE 4

UV Probe Analysis vs. HPLC Analysis of Dissolution Samples

| | Batch # | | | |
|---|---|---|---|---|
| | 100-15021 | | 100-15022 | |
| | Quantitation | | | |
| Time (hours) | UV Probe % Released | HPLC % Released | UV Probe % Released | HPLC % Released |
| 1 | 73.78% | 73.0% | 78.84% | 73.4% |
| 2 | 84.32% | 87.6% | 86.23% | 88.5% |

TABLE 4-continued

UV Probe Analysis vs. HPLC Analysis of Dissolution Samples

| | Batch # | | | |
|---|---|---|---|---|
| | 100-15021 | | 100-15022 | |
| | Quantitation | | | |
| Time (hours) | UV Probe % Released | HPLC % Released | UV Probe % Released | HPLC % Released |
| 4 | 94.11% | 95.8% | 94.52% | 94.5% |
| 6 | 98.03% | 98.0% | 97.09% | 96.3% |

The dissolution data for the prototype tablets reveal the Series 1 formulations to have the greatest differentiation among the dissolution profiles at the early time points.

The Series 2 formulations display a slighter differentiation at these time points for the range of SR/IR layer weight ratios.

REFERENCES

Kim S S, Lee H W, Lee K T. Validated method for determination of mazindol in human plasma by liquid chromatography/tandem mass spectrometry. *J Chromatogr B Analyt Technol Biomed Life Sci.* 2009; 877:1011-16.

Barbaresi W J et al: How common is attention-deficit/hyperactivity disorder? Incidence in a population-based birth cohort in Rochester, Minn. *Arch Pediatr Adolesc Med.* 2002; 156(3):217-224.

Kessler R C et al: The prevalence and correlates of adult ADHD in the United States: results from the National Comorbidity Survey Replication. *American Journal of Psychiatry.* 2006, 163(4):716-723.

Faraone S V, Glatt S J: A comparison of the efficacy of medications for adult attention-deficit/hyperactivity disorder using meta-analysis of effect sizes. *J Clin Psychiatry.* 2009; 71(6):754-763.

Fallingborg J Intraluminal pH of the human gastrointestinal tract. Dan Med Bull. 1999 June; 46(3):183-96. Greenhill L L, et al: Medication treatment strategies in the MTA Study: relevance to clinicians and researchers. *J Am Acad Child Adolesc Psychiatry.* 1996; 35(10):1304-1313.

Antshel K M, et al: Advances in understanding and treating ADHD. *BMC Medicine.* 2011; 9:72-84.

Moffitt T E, et al: Is Adult ADHD a Childhood-Onset Neurodevelopmental Disorder? Evidence From a Four-Decade Longitudinal Cohort Study. *Am J Psychiatry.* 2015: appiajp201514101266 (ePub ahead of print).

Kooij S J, et al: European consensus statement on diagnosis and treatment of adult ADHD: the European Network Adult ADHD. *BMC Psychiatry.* 2010; 10:67

Konofal, Eric et al. "Pilot Phase II Study of Mazindol in Children with Attention Deficit/hyperactivity Disorder." *Drug Design, Development and Therapy* 8 (2014): 2321-2332.

Kidane et al., International Publication No. WO2001/123496, published on Oct. 6, 2011.

The invention claimed is:

1. A mazindol oral pharmaceutical unit dosage form in the form of a multilayer matrix-type tablet comprising:
at least one immediate-release (IR) layer comprising mazindol and at least one diluent,
at least one sustained-release (SR) layer comprising mazindol and at least one sustained-release, pH-independent and water-insoluble polymer,
for a total amount of mazindol ranging from 1 to 6 mg and a ratio of mazindol in weight between the IR layers and the SR layers ranging from 40:60 to 80:20.

2. The unit dosage form according to claim 1, with a dissolution of between 60% and 80% at 1 hour, of between 70% and 90% at 2 hours, as measured according to the US Pharmacopeia Method 2 using a rotating blade method at 50 rpm in a 500 ml dissolution medium of 0.01 N HCl.

3. The unit dosage form according to claim 1, wherein the total weight of the unit dosage form ranges from 50 to 200 mg.

4. The unit dosage form according to claim 3, wherein the total weight of the unit dosage form is 100 mg.

5. The unit dosage form according to claim 1, wherein the diluent in said IR layers is selected in the group consisting of lactose, anhydrous lactose, spray-dried lactose, calcium carbonate, calcium sulfate, calcium sulfate dehydrate, calcium lactate trihydrate, monobasic calcium sulfate monohydrate, calcium carbonate, tribasic calcium phosphate, diabasic calcium phosphate, compressible sugars, dextrates, dextrin, dextrose, calcium phosphate, kaolin, magnesium carbonate, magnesium oxide, maltodextrin, mannitol, powdered cellulose, starch, modified starch, starch hydrolyzates, pregelatinized starch, microcrystalline cellulose, powdered cellulose, cellulose and cellulose derivatives, hydroxypropylmethylcellulose, hydroxypropylmethylcellulose and sucrose.

6. The unit dosage form according to claim 1, wherein the sustained-release, pH-independent and water insoluble polymer is said SR layers is selected from the group consisting of cellulose polymers, high-molecular weight polymers of acrylic acid that are crosslinked with either allyl sucrose or allyl ethers of pentaerythritol (carbomers), polymers from the class of methacrylic acids, polyvinylalcohol derivatives, polymers of lactic and glycolic acids (PLGA), starches, waxes, polyvinyl acetate derivatives, polyvinylpyrrolidone derivatives and mixtures thereof.

7. The unit dosage form according to claim 1, further comprising a lubricant in each layer.

8. The unit dosage form according to claim 1, wherein said unit dosage form is capable of maintaining a steady-state mazindol plasma concentration in vivo at a reduced fluctuation above 40% of the Cmax(ss) value for at least 12 h.

9. The unit dosage form according to claim 8, wherein the reduced fluctuation is above 60% of the Cmax(ss) value.

10. The unit dosage form according to claim 1, for its use as medicinal product administered in repeat once-a-day form via oral route.

11. The unit dosage form according to claim 1, for use for treating attention deficit disorders (ADD) or attention deficit/hyperactivity disorder (ADHD) or related deficit of alertness or decline of vigilance or excessive daytime sleepiness.

12. The unit dosage form according to claim 11, for treating narcolepsy or idiopathic hypersomnia.

13. The unit dosage form according to claim 1, for use in combination with iron as a combination product for simultaneous, separate or sequential use.

14. The unit dosage form according to claim 11, for treating attention deficit disorders (ADD) or attention deficit/hyperactivity disorder (ADHD) or related deficit of alertness or decline of vigilance or excessive daytime sleepiness.

15. The unit dosage form according to claim 1, for use in combination with a psychostimulant as a combination product for simultaneous, separate or sequential use.

16. The unit dosage form according to claim 15, for treating attention deficit disorders (ADD) or attention deficit/hyperactivity disorder (ADHD) or related deficit of alertness or decline of vigilance or excessive daytime sleepiness.

17. The unit dosage form according to claim 1, wherein the weight ratio ranges from 50:50 to 70:30.

18. The unit dosage form according to claim 1, wherein the weight ratio is 50:50.

19. The unit dosage form according to claim 1, wherein the SR layer comprises a hydrophilic matrix.

20. A process for preparing the unit dosage form according to claim 1, comprising:
  (a) preparing the blend of the excipients of the IR layers,
  (a') preparing the blend of the excipients of the SR layers,
  (b) adding the IR blend of step (a) and the SR blend of step (a') into a multilayer tablet press.

21. The process according to claim 20, wherein the multilayer tablet press is a bilayer tablet press.

\* \* \* \* \*